United States Patent [19]

Powers

[11] Patent Number: 5,278,323
[45] Date of Patent: Jan. 11, 1994

[54] PROCESS FOR PREPARING CHIRAL DIBENZOFURANS VIA INTRAMOLECULAR HECK REACTION

[75] Inventor: Matthew R. Powers, Barto, Pa.

[73] Assignee: Rhone-Poulenc Rorer Pharmaceuticals Inc., Collegeville, Pa.

[21] Appl. No.: 54,983

[22] Filed: Apr. 30, 1993

[51] Int. Cl.$^5$ .......................................... C07D 307/91
[52] U.S. Cl. ..................................................... 549/461
[58] Field of Search ............................................. 549/461

[56] References Cited

U.S. PATENT DOCUMENTS 4,863,921  4/1988  Youssefyeh et al. ............. 514/230.5

OTHER PUBLICATIONS

Youssefyeh et al., J. Med. Chem., vol. 35, pp. 895–903 (1992).
Matharu et al., J. Med. Chem., vol. 20, pp. 197–204 (1977).
Youssefyeh et al., J. Med. Chem., vol. 35, pp. 903–911 (1992).
Toth et al., J. Org. Chem., vol. 52(3), pp. 473–475 (1987).
Chem. Abstracts, vol. 96:19951q (1982).
Chem. Abstracts, vol. 96:142869n (1982).
Chem. Abstracts, vol. 68:21826t (1968).

*Primary Examiner*—Bernard Dentz
*Attorney, Agent, or Firm*—James A. Nicholson; Martin F. Savitzky; Raymond S. Parker, III

[57] ABSTRACT

The present invention is directed to the synthesis of 2-chloro-cis-[5a(S)-9a(S)-(5a,6,7,8,9,9a-hexahydro)]-dibenzofuran-4-carboxylic acid by an intramolecular Heck stereospecific synthesis substantially free of undesirable 8-chloro-2,6-methano-2H-3,4,5,6-tetrahydro-1-benzoxocin-10-carboxylic.

5 Claims, No Drawings

PROCESS FOR PREPARING CHIRAL DIBENZOFURANS VIA INTRAMOLECULAR HECK REACTION

BACKGROUND OF THE INVENTION

The tetra and hexahydrodibenzofuran ring systems are common in biologically active natural compounds (Toth, J. E., et al. J. Org. Chem. 1987, 52, 473). Analogs containing these structural features have been studied for a variety of indications, such as: antipsychotics (Busch, N., et al. French Patent 2 482 966, 1981), analgesics (Skaletzky, L. L. U.S. Pat. No. 3,317,527, 1967), antitussives (Matharu, S. S.; et al. J. Med. Chem. 1977, 20, 197), CNS stimulants (Skaletzky, L. L. U.S. Pat. No. 3,317,527, 1967), and antiemetics (Youssefyeh, R. D., et al. J. Med. Chem. 1992, 35, 895).

Methods for obtaining these ring systems therefore are of considerable interest. Among the reported compounds which have valuable antiemetic and antipsychotic properties is 4-[N-(1-azabicyclo[2.2.2]octan-3-yl)]-2-chloro[5a,6,7,8,9,9a-hexahydro]dibenzofurancarboxamide. This racemic compound has eight possible stereoisomers, and it has been reported that 4-[N-(1-azabicyclo-[2.2.2]octan-3(S)-yl]-2-chloro-[5a(S)-9a(S)-(5a,6,7,8,9,9a-hexahydro)]-dibenzofurancarboxamide is the most active of the isomers. This is shown by Formula I.

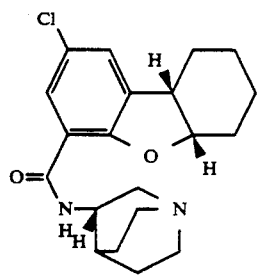

Formula 1

The compound of Formula I is prepared by the reaction of 2-chloro-5a,6,7,8,9,9a-hexahydrodibenzofuran-4-carboxylic acid with 3-aminoquinuclidine and is described in U.S. Pat. No. 4,863,921.

REPORTED DEVELOPMENTS

Of interest is the synthesis of both enantiomers but the synthesis of the S,S enantiomer of 2-chloro-cis-(5a,6,7,8,9,9a-hexahydro)]dibenzofuran-4-carboxylic acid is particularly interesting. Synthesis of these isomers has been reported using semipreparative chiral HPLC and classical resolution (Youssefyeh, R. D.; et al J. Med. Chem. 1992, 35, 903).

The above reported synthesis is described by the following Scheme I.

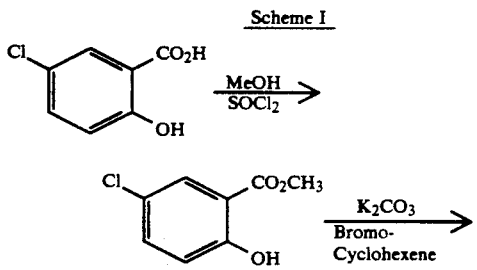

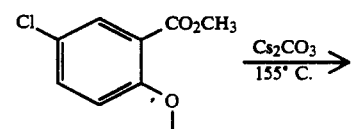

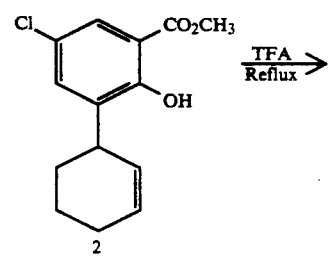

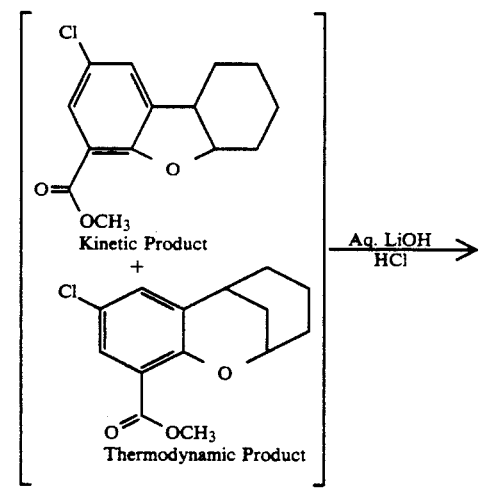

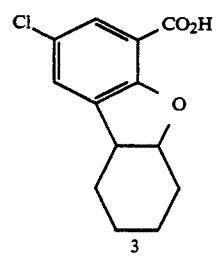

This starts with an alkylation of methyl 5-chlorosalicylate with 3-bromocyclohexene to afford methyl 5-chloro-2-(3'-cyclohexenyl)salicylate (1). After a thermal Claisen rearrangement is performed to afford methyl 5-chloro-3-(3'-cyclohexenyl (2) an intramolecular cyclization with trifluroacetic acid followed by hydrolysis yields racemic 2-chloro-cis-(5a,6,7,8,9,9a-hexahydro)]-dibenzofurancarboxylic acid and also results in the formation of a thermo-dynamically favored product, 8-chloro-2,6-methano-2H-3,4,5,6-tetrahydro-1-benzoxocin-10-carboxylic acid. The chiral acids are then obtained by fractional recrystallization as the R or S α-methylbenzylamine salt. This is a 7 step synthesis.

A second procedure for obtaining 2-chloro-cis-[5a(S)-9a(S)-(5a,6,7,8,9,9a-hexahydro)]dibenzofuran-4-carboxylic acid is by the transfer of chirality in a Claisen rearrangements. This is described in the following Scheme II.

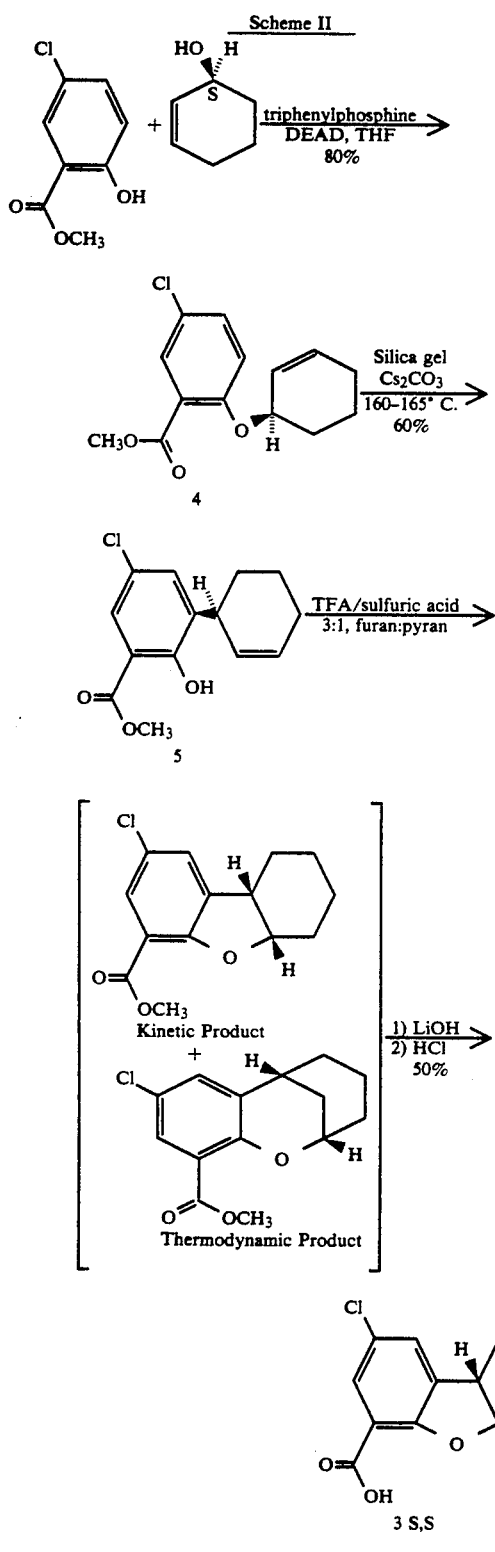

This is a more direct approach to obtain a stereospecific synthesis and describes the Claisen rearrangement with a chiral ether (4). S-2-Cyclohexene-1-ol was obtained by asymmetric ring opening of cyclohexene oxide. A Mitsunobu condensation between S-cyclohexanol and methyl 5-chlorosalicylate provided the chiral ether 4. The thermal Claisen rearrangement of 4 afforded 5 in moderate yield along with the products of elimination, cyclohexadiene and methyl 5-chloro-salicylate. Acid catalyzed intramolecular cyclization yielded a 3 to 1 mixture of structural isomers shown in Scheme II. The benzofuran isomer is the kinetic product and can be converted to the thermodynamically favored benzoxocin isomer by treatment with concentrated sulfuric acid as reported earlier (R. D. Youssefyeh et al. J. Med. Chem. 1992, 35, 903). Upon hydrolysis with lithium hydroxide the benzofuran isomer precipitates out as the lithium salt and is easily separated by filtration. Acidification of this material yields 2-chloro-[5a(S)-9a(S)-(5a,6,7,8,9,9a-hexahydro)]dibenzofuran-4-carboxylic acid (3 S,S) in 5 steps, which is similar to the material obtained by classical resolution, the structural determination of which was made by X-ray crystallography. The Claisen rearrangement using S-cyclohexanol proceeds in only moderate yield, and one quarter to one third of the chiral material obtained is lost as the benzopyran isomer.

The present invention is directed to the synthesis of 2-chloro-cis-[5a(S)-9a(S)-(5a,6,7,8,9,9a-hexahydro)]-dibenzofuran-4-carboxylic acid by stereospecific synthesis to obtain the desired isomer.

SUMMARY OF THE INVENTION

We have discovered that the desired 2-chloro-cis-[5a(S)-9a(S)-(5a,6,7,8,9,9a-hexahydro)]-dibenzofurancarboxylic acid may be conveniently prepared substantially free of undesirable 8-chloro-2,6-methano-2H-3,4,5,6-tetrahydro-1-benzoxocin-10-carboxylic acid by an intramolecular Heck reaction to obtain a cis fused benzofuran system.

DETAILED DESCRIPTION

Intramolecular Heck synthesis substantially eliminates the benzoxocine structural isomer and is described by Scheme III below.

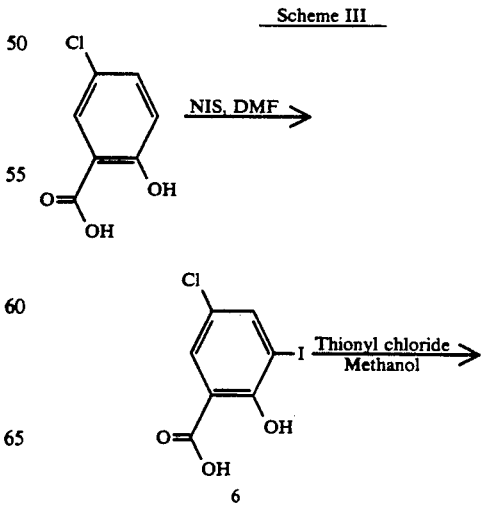

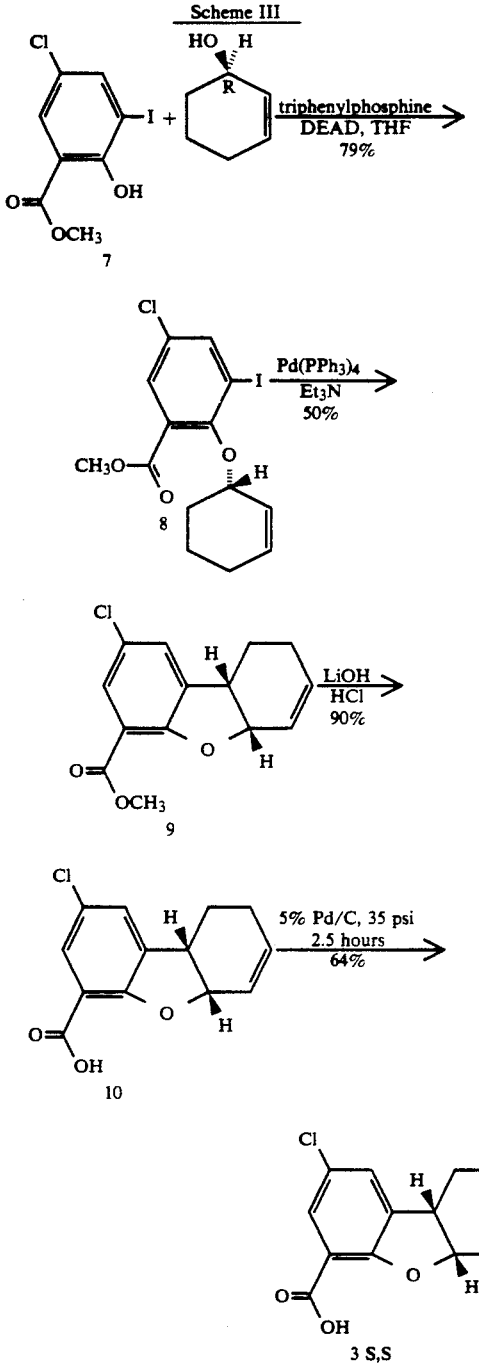

The process is stereospecific by using a chiral ether. 5-Chlorosalicylic acid is iodinated in the 3 position with N-iodosuccinamide in DMF and esterified with thionyl chloride in methanol to afford 7. The Mitsunobu condensation of 7 with R-2-cyclohexen-1-ol yields the chiral ether 8 which can be cyclized via an intramolecular Heck reaction to afford 9 with retention of chirality. Lithium hydroxide hydrolysis of 9 followed by reduction with 5% palladium on carbon yields 2-chloro-[5a(S)-9a(S)-(5a, 6,7,8,9,9a-hexahydro)]dibenzofuran-4-carboxylic acid (3 S,S) in 6 steps. This results in a stereospecific synthesis and eliminates the presence of the benzoxocine isomer.

The following reaction examples describe the process of this invention and are intended to be representative and not to limit the reaction conditions involved.

5-Chloro-3-iodosalicylic Acid (6)

5-Chlorosalicylic acid (20 g, 115.8 mmol) is dissolved in DMF (100 mL). To this solution is added NIS (26.1 g, 116.0 mmol) which causes the reaction to warm up to 60° C. The reaction is stirred at room temperature for 20 hours. At this point ethyl acetate (100 mL) is added and the solution washed with 0.1N HCl (100 mL). The organic phase is then washed with water (3×100 mL), dried with sodium sulfate and evaporated under reduced pressure to yield 5-chloro-3-iodosalicylic acid as off-white solid. (mp 160°-163° C.)

Methyl 5-chloro-3-iodosalicylate (7)

Thionyl chloride (30 mL, 411 mmol) is added dropwise to methanol (100 mL) in an ice bath. The addition is controlled to hold the temperature at 25° C. Upon completion of the addition 6 (25 g, 84 mmol) is added and the reaction heated to reflux for 4 hours. The solids dissolve at first then after 2 hours solids start to come out of solution. After 4 hours TLC (hex: EtOAc; 9:1) shows no starting material. The reaction is cooled in the refrigerator for 12h. The solids formed are filtered washed with water (30 mL), and dried under vacuum at 27° C. to yield methyl 5-chloro-3-iodosalicylate as an off white solid. (mp 143°-145° C.)

Methyl-5-chloro-3-iodo-2-(1'S-cyclohex-2-enyl)salicylate (8)

Methyl 5-chloro-3-iodosalicylate (1.5 g, 4.8 mmol) and triphenylphosphine (1.53 g, 5.7 mmol) are placed in a dry 3 neck flask and anhydrous THF (20 mL) is added by cannula under nitrogen pressure. R-2-cyclohexen-1-ol (0.48 g, 4.8 mmol) is added by syringe and the reaction cooled to 0° C. A solution of THF (5 mL) and diethylazodicarboxylate (0.91 g, 4.8 mmol) is added dropwise over 1 hour, holding the temperature at 0° C. The reaction is held at 0° C. for 30 minutes after the addition and then allowed to warm to room temperature. Stirring is continued for 3 hours. Evaporation of the solvent under reduced pressure results in methyl-5-chloro-3-iodo-2-(1'S-cyclohex-2-enyl)salicylate which is used directly in the next step.

Methyl-2-Chloro-5a(S),9a(S)-5a,8,9,9a-tetrahydrodibenzofuran-4-carboxylate (9)

The ether 8 (1.1 g, 2.7 mmol) is dissolved in THF (10 mL) and acetonitrile (10 mL). Tetrakistriphenylphosphinepalladium(0) (0.47 g, 0.41 mmol) and triethylamine (0.8 mL) are added to the solution and it is heated to reflux for 16 hours. The reaction is cooled to 25° C. and water (30 mL) is added. This solution is extracted with ether (2×50 mL). The ether extracts are combined, filtered and washed with saturated sodium bicarbonate (100 mL) and water (100 mL). The organic layer is then dried over magnesium sulfate, filtered, and evaporated under reduced pressure to yield Methyl-2-Chloro-5a(S)-,9a(S)-5a,8,9,9a-tetrahydrodibenzofuran-4-carboxylate.

2-Chloro-5a(S),9a(S)-5a,8,9,9a-tetrahydrodibenzofuran-4-carboxylic acid (10)

To a slurry of 9 (0.7 g, 206 mmol) in water (15 mL) is added lithium hydroxide monohydrate (0.16 g, 3.7 mmol) and the mixture heated to 65° C. When no more starting material remains by TLC (Hex: EtOAc; 9:1), the mixture is cooled overnight in the refrigerator. The precipitated solids are filtered and then slurried in ethyl acetate (10 mL). Deionized water (5 mL) is added to this slurry, which is then acidified with 10% aqueous hydrochloric acid to a pH of 1-2. The layers are separated and the ethyl acetate phase concentrated to dryness to give methyl-2-chloro-5a(S),9a(S)-5a,8,9,9a-tetrahydrodibenzofuran-4-carboxylic acid.

2-Chloro-[5a(S)-9a(S)-(5a,6,7,8,9,9a-hexahydro)]dibenzofuran-4-carboxylic acid (3 S,S)

The acid 10 (0.5 g, 2.0 mmol) is slurried in (15 mL) of ethanol in a Parr shaker reaction bottle. 5% Palladium on carbon (0.05 g) is added to this and the reaction placed on a Parr shaker. The reaction flask is evacuated and flushed with nitrogen three times then flushed with hydrogen twice before being filled to 35 psi with hydrogen. The reaction is run for 2.5 h. The reaction mixture is filtered through a frit and the catalyst is washed with ethanol (25 mL). The solvent is evaporated under reduced pressure, this material is then dissolved in hexane (1 mL), cooled to 5° C. and filtered to yield 2-chloro-[5a(S)-9a(S)-(5a,6,7,8,9,9a-hexahydro)]-dibenzofuran-4-carboxylic acid (m.p. 150°-154° C.).

We claim:

1. A process for the preparation of 2-chloro-cis-[5a(S)-9a(S)-(5a,6,7,8,9,9a-hexahydro)]dibenzofurancarboxylic acid substantially free of benzoxocine isomer by reducing 2-chloro-5a(S),9a(S)-5a,8,9,9a-tetrahydrodibenzofuran-4-carboxylic acid.

2. A process according to claim 1 which preliminarily includes the step of hydrolyzing methyl-2-chloro-5a(S)-,9a(S)-5a,8,9,9a-tetrahydrodibenzofuran-4-carboxylate with lithium hydroxide monohydrate to obtain 2-chloro-5a(S),9a(S)-5a,8,9,9a-tetrahydro-dibenzofuran-4-carboxylic acid 3. A process according to claim 2 which preliminarily includes the step of heating methyl-5-chloro-3-iodo-2-(1'S-cyclohex-2-enyl)salicylate with tetrakistriphenylphosphinepalladium(0) in the presence of an amine to obtain methyl-2-chloro-5a(S),9a(S)-5a,8,9,9a-tetrahydro-dibenzofuran-4-carboxylate 4. A process according to claim 3 which preliminarily includes the step of condensing methyl 5-chloro-3-iodosalicylate with R-2-cyclohexen-1-ol in the presence of triphenyl-phosphine and diethylazodicarboxylate to obtain methyl-5-chloro-3-iodo-2-(1'S-cyclohex-2-enyl)-salicylate.

5. A process for the preparation of substantially pure 2-chloro-cis-[5a(S)-9a(S)-(5a,6,7,8,9,9a-hexahydro)]-dibenzofuran-4-carboxylic acid by:
   (a) condensing methyl 5-chloro-3-iodosalicylate with R-2-cyclohexen-1-ol in the presence of triphenylphosphine and diethylazodicarboxylate to obtain methyl-5-chloro-3-iodo-2-(1'S-cyclohex-2-enyl)-salicylate;
   (b) heating said methyl-5-chloro-3-iodo-2-(1'S-cyclohex-2-enyl)salicylate with tetrakistriphenylphosphinepalladium(0) in the presence of an amine to obtain methyl-2-chloro-5a(S),9a(S)-5a,8,9,9a-tetrahydro-dibenzofuran-4-carboxylate;
   (c) hydrolyzing said methyl-2-chloro-5a(S),9a(S)-5a,8,9,9a-tetrahydrodibenzofuran-4-carboxylate with lithium hydroxide monohydrate to obtain 2-chloro-5a(S),9a(S)-5a,8,9,9a-tetrahydrodibenzofuran-4-carboxylic acid; and
   (d) reducing said 2-chloro-5a(S),9a(S)-5a,8,9,9a-tetrahydrodibenzofuran-4-carboxylic acid to obtain 2-chloro-[5a(S)-9a(S)-(5a,6,7,8,9,9a-hexahydro)]-dibenzofuran-4-carboxylic acid.

* * * * *